(12) United States Patent
Reineke et al.

(10) Patent No.: US 11,045,164 B2
(45) Date of Patent: Jun. 29, 2021

(54) NONINVASIVE FLUID AND ELECTROLYTE BALANCE MONITOR

(71) Applicants: Boston Scientific Scimed, Inc., Maple Grove, MN (US); Regents of University of Minnesota, Minneapolis, MN (US)

(72) Inventors: Jeffrey W. Reineke, Vadnais Heights, MN (US); Andrew D. Bicek, Elk River, MN (US); John R. Ballard, Saint Bonifacius, MN (US)

(73) Assignees: BOSTON SCIENTIFIC SCIMED, INC., Maple Grove, MN (US); REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 1233 days.

(21) Appl. No.: 15/004,580

(22) Filed: Jan. 22, 2016

(65) Prior Publication Data

US 2016/0213348 A1 Jul. 28, 2016

Related U.S. Application Data

(60) Provisional application No. 62/106,373, filed on Jan. 22, 2015.

(51) Int. Cl.
*A61B 8/08* (2006.01)
*A61B 8/00* (2006.01)
(Continued)

(52) U.S. Cl.
CPC .............. *A61B 8/08* (2013.01); *A61B 5/0537* (2013.01); *A61B 5/4875* (2013.01);
(Continued)

(58) Field of Classification Search
CPC ....... A61B 8/08; A61B 8/4209; A61B 5/4875; A61B 5/0537; A61B 8/5223;
(Continued)

(56) References Cited

U.S. PATENT DOCUMENTS 2,146,933 A * 2/1939 Budin .................. A61H 1/0218
602/22
5,935,066 A 8/1999 Harris
(Continued)

FOREIGN PATENT DOCUMENTS

WO 2010149984 12/2010

OTHER PUBLICATIONS

Hoffer, E. C., Meador, C. K., & Simpson, D. C. Correlation of whole-body impedance with total body water volume. (1969). Journal of applied physiology, 27(4), 531-534. (Year: 1969).*
(Continued)

*Primary Examiner* — James M Kish
(74) *Attorney, Agent, or Firm* — Kacvinsky Daisak Bluni PLLC

(57) ABSTRACT

Systems and methods for the assessment of fluid content and electrolyte balance in patients are provided. The systems generally include two or more ultrasound transducers and may include impedance-sensing electrodes as well. These elements are positioned about a soft tissue of a patient by means of a retention element.

16 Claims, 8 Drawing Sheets

(51) Int. Cl.
*A61B 5/0537* (2021.01)
*A61B 5/00* (2006.01)

(52) U.S. Cl.
CPC .......... *A61B 8/4227* (2013.01); *A61B 8/4236* (2013.01); *A61B 8/4427* (2013.01); *A61B 8/4477* (2013.01); *A61B 8/5223* (2013.01); *A61B 5/4878* (2013.01); *A61B 5/6824* (2013.01); *A61B 5/6828* (2013.01); *A61B 8/40* (2013.01)

(58) Field of Classification Search
CPC ... A61B 8/4427; A61B 8/4236; A61B 8/4227; A61B 8/4477; A61B 5/6824; A61B 5/4878; A61B 5/6828; A61B 8/40; A61B 5/14546; A61B 5/4869
See application file for complete search history.

(56) References Cited

U.S. PATENT DOCUMENTS

| | | | | | |
|---|---|---|---|---|---|
| 6,398,734 | B1* | 6/2002 | Cimochowski | ...... | A61B 5/0031 600/454 |
| 7,033,321 | B1* | 4/2006 | Sarvazyan | ............ | A61B 5/411 600/449 |
| 7,291,109 | B1* | 11/2007 | Sarvazyan | ............ | A61B 5/411 600/438 |
| 2002/0111568 | A1* | 8/2002 | Bukshpan | ................ | A61B 8/12 601/2 |
| 2003/0093117 | A1* | 5/2003 | Saadat | ................ | A61B 5/4238 606/221 |
| 2003/0163055 | A1* | 8/2003 | McLaughlin | ........ | A61B 5/0285 600/504 |
| 2007/0066897 | A1* | 3/2007 | Sekins | ................... | A61B 5/445 600/437 |
| 2008/0021325 | A1* | 1/2008 | Drost | .................... | A61B 5/021 600/454 |
| 2010/0174186 | A1* | 7/2010 | Cohen-Solal | ........ | A61B 5/0051 600/438 |
| 2010/0234716 | A1* | 9/2010 | Engel | .................. | A61B 5/02055 600/391 |
| 2011/0130688 | A1* | 6/2011 | Nakamura | ........... | A61B 5/0053 601/2 |
| 2013/0111665 | A1* | 5/2013 | Duesdieker | .............. | A61B 5/70 5/601 |
| 2014/0221792 | A1* | 8/2014 | Miller | .................. | A61B 5/4875 600/309 |

OTHER PUBLICATIONS

Sarvazyan a et al, "Ultrasonic assessment of tissue hydration status", Ultrasonics, IPC Science and Technology Press Ltd. Guildford, (2005), vol. 43, pp. 661-671.

* cited by examiner

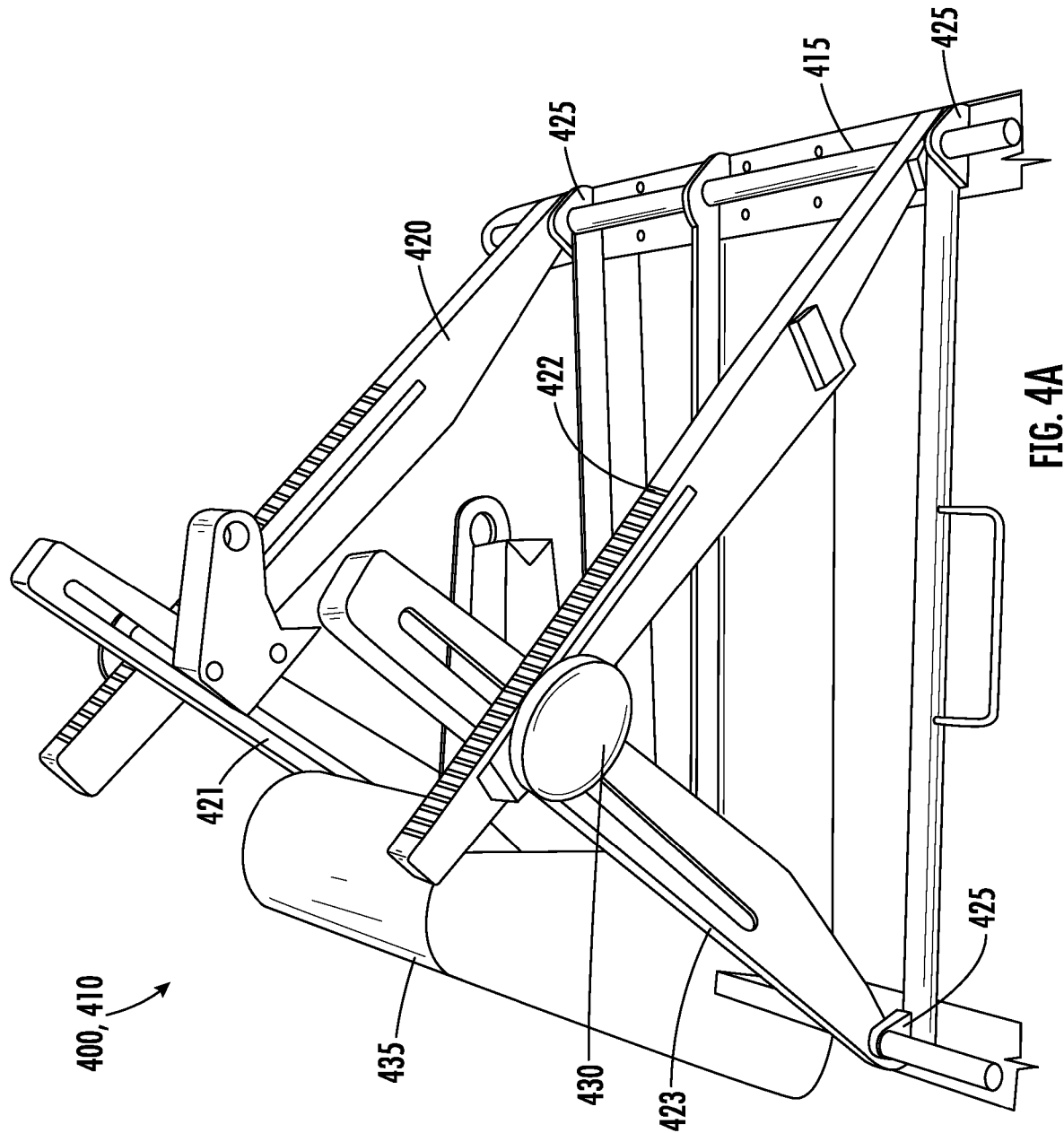

NONINVASIVE FLUID AND ELECTROLYTE BALANCE MONITOR

CROSS-REFERENCE TO RELATED APPLICATIONS

This application claims the benefit of priority under 35 U.S.C. § 119 to U.S. Provisional Patent Application No. 62/106,373 titled "NONINVASIVE FLUID AND ELECTROLYTE BALANCE MONITOR" by Ballard, et al. and filed Jan. 22, 2015, which is incorporated by reference in its entirety and for all purposes.

FIELD OF THE INVENTION

This application relates to the field of medical devices and medical procedures. More particularly, the application is related to devices and methods for noninvasive assessment of fluids and electrolytes in bodily tissues.

BACKGROUND

Human tissues are, generally, 70-80% water. The precise amount of water within tissues, as well as their specific electrolyte content, can vary during exertion or rest, due to changes in dietary fluid or salt intake, or due to disease. Accordingly, information on fluid content and/or electrolyte content can shed light on specific acute or chronic diseases or normal physiologic processes.

For instance, peripheral edema is a clinical sign of excess fluid volume within tissues between cells which may be caused by a wide variety of conditions, including chronic heart and/or renal failure, joint disease, pregnancy, excessive salt intake, physical tiredness, etc. Treatment of peripheral edema includes sodium restriction, diuretic use, and appropriate management of the underlying disorder, though in some cases simple elevation of affected body tissues may suffice. Currently, edemas are diagnosed by visual observation, or by a qualitative assessment of the depth of an indentation made by finger pressure over a bony prominence. In some cases, edemas are also characterized by imaging using computer tomography, magnetic resonance, or peripheral lymphography. It should be noted, however, that these imaging methods are not generally used for routine characterization of edemas, despite the advantages they hold for more precise characterization of the condition.

Two additional means of estimating body fluid content measurement are ultrasound velocity and impedance. Experimental work dating back to the 1950s has measured the ultrasound velocities in skeletal muscle in the range of 1550-1630 m/s. While anisotropy and muscle fiber orientation have very little effect on the ultrasound velocity, changes in water and fat content contribute to changes in ultrasound velocity. Tissue impedance, meanwhile, has been used to measure body fat and body water content since at least 1990. Despite the long established use of these technologies in laboratory and other settings, they have not been used together in clinical settings for fluid monitoring.

Electrolyte concentration, unlike edematous fluid accumulation, is typically assessed more invasively, by analysis of venous blood. Consequently, real-time characterization of electrolyte concentration is not possible in most clinical settings.

SUMMARY OF THE INVENTION

The present invention, in its various aspects, meets an ongoing need in the field for rapid, noninvasive, and simultaneous assessment of fluid and electrolyte content of tissues by utilizing compact and easily deployed sensors.

In one aspect, the present invention relates to a system for assessing fluid content in a patient which includes two or more ultrasound transducers separated from one another by at least one fixed distance, as well as a retention element housing the ultrasound transducers and (optionally) an ultrasound reflector that is moveable to permit it to be positioned opposite the transducers when the retention element is placed about at least part of the circumference of a body or soft tissue of a patient. In various embodiments, the retention element is a cuff sized for placement about the circumference of the soft tissue, an adhesive patch or a caliper. In some cases, the retention element is, or connects to, a positioning accessory that includes a base, a plurality of crossmembers, each being rotatably or flexibly attached to the base, and moveable clamp for coupling at least two of the plurality of crossmembers to one another. At least one of the crossmembers includes a slot through which the moveable clamp can be inserted, and a plurality of markings along the length of the slot.

The system also optionally includes a plurality of electrodes for impedance measurements, which electrodes can be disposed in the retention element. In some cases, the system includes three ultrasound transducers, each separated by the fixed distance, and/or the reflector is slidably disposed along an interior of the retention element. The system is also optionally usable in medicine.

In another aspect, the present invention relates to a method of assessing a patient using a system as described above. The method includes measuring at least one ultrasound echo time with the ultrasound transducers, calculating a speed of sound through the soft tissue of the patient based on the echo time(s), and calculating a fluid content of the soft tissue based on the calculated speed of sound. In instances where the system includes electrodes for sensing impedance, the method includes the foregoing steps, plus the additional steps of measuring a tissue impedance and, based on the calculated fluid content and the measured tissue impedance, estimating an electrolyte content of the tissue. This may be done by contacting the patient with two measurement electrodes and/or the application of an adaptive algorithm. The step of measuring the speed of sound through the tissue also optionally includes detecting a sound generated by the body of the patient (optionally an event in the heart) by means of a plurality of piezoelectric detectors on the body surface of the patient, which detectors are separated by a fixed distance.

In another aspect, the present invention relates to a method of assessing the patient that includes measuring a speed of sound through a soft tissue of the patient by placing a device with at least two ultrasound transducers separated by a fixed distance about at least a portion of the circumference of the patient's body, energizing the transducers to produce a plurality of ultrasound echoes and measure a plurality of ultrasound echo times, then calculating based on the ultrasound echo times and the fixed distance, a speed of sound through the soft tissue of the patient. The method also preferably (but not necessarily) includes the steps of measuring an impedance of a soft tissue of the patient and calculating an electrolyte balance based on the calculated impedance and speed of sound. In various embodiments, the method utilizes a device or system according to one or more of the embodiments described above.

In another aspect, the present invention relates to a system for assessing fluid content and electrolyte balance in a patient that includes two or more ultrasound transducers, a plurality of impedance measurement electrodes and a retention element housing the transducers. The retention element can be a caliper, in which case an ultrasound transducer can be placed at the end of each arm. The retention element can also be connected to the impedance electrodes. In some cases, the system includes three ultrasound transducers separate by a fixed distance from one another. The device can also include an ultrasound reflector that is moveable to permit placement opposite the ultrasound transducers, and the reflector may be slidably disposed along an interior of the retention element.

In yet another aspect, the present invention relates to a method of assessing fluid content and electrolyte balance of a patient that includes the steps of a method of assessing a patient comprising the steps of measuring a speed of sound through a tissue, estimating a fluid content of the tissue based on the speed of sound through the tissue, measuring a tissue impedance, and based on the estimated fluid content and the measured tissue impedance, estimating an electrolyte content of the tissue. In this aspect of the invention, the step of measuring a speed of sound through the tissue includes detecting a sound generated by the body of the patient using a plurality of piezoelectric detectors on a surface of the body on the patient, each of the plurality of piezoelectric detectors being separated from one another by a fixed distance. The method can include a step of detecting an event within the body of the patient which generates the sound. The event can be inside of the heart of the patient.

And in still another aspect, the present invention relates to a system for ultrasound fluid measurement that includes a positioning accessory comprising a base, a plurality of crossmembers, each rotatably or flexibly coupled to opposite ends of the base, and a moveable clamp for coupling at least two of the plurality of crossmembers to one another. At least one of the crossmembers includes a slot through which the moveable clamp is insertable and a plurality of markings along a length of the slot. In some cases, the positioning accessory includes two pairs of crossmembers, each pair coupled by a moveable clamp inserted through slots in each of the paired cross member, and each crossmember including a plurality of markings along the length of the slot. The positioning accessory also optionally includes a movable, height adjustable structure moveably coupled to the base for supporting a limb of a patient during a measurement. In some cases, the clamp or clamps couple directly to an ultrasound transducer or transducer assembly, and/or to a reflector. In other cases, the clamp or clamps couple to an assembly (optionally a rigid body sized to extend about at least a portion of a circumference of a limb of a patient) that in turn couples to the transducer, transducer assembly and/or reflector.

DRAWINGS

Aspects of the invention are described below with reference to the following drawings in which like numerals reference like elements, and wherein.

Figure 2A:
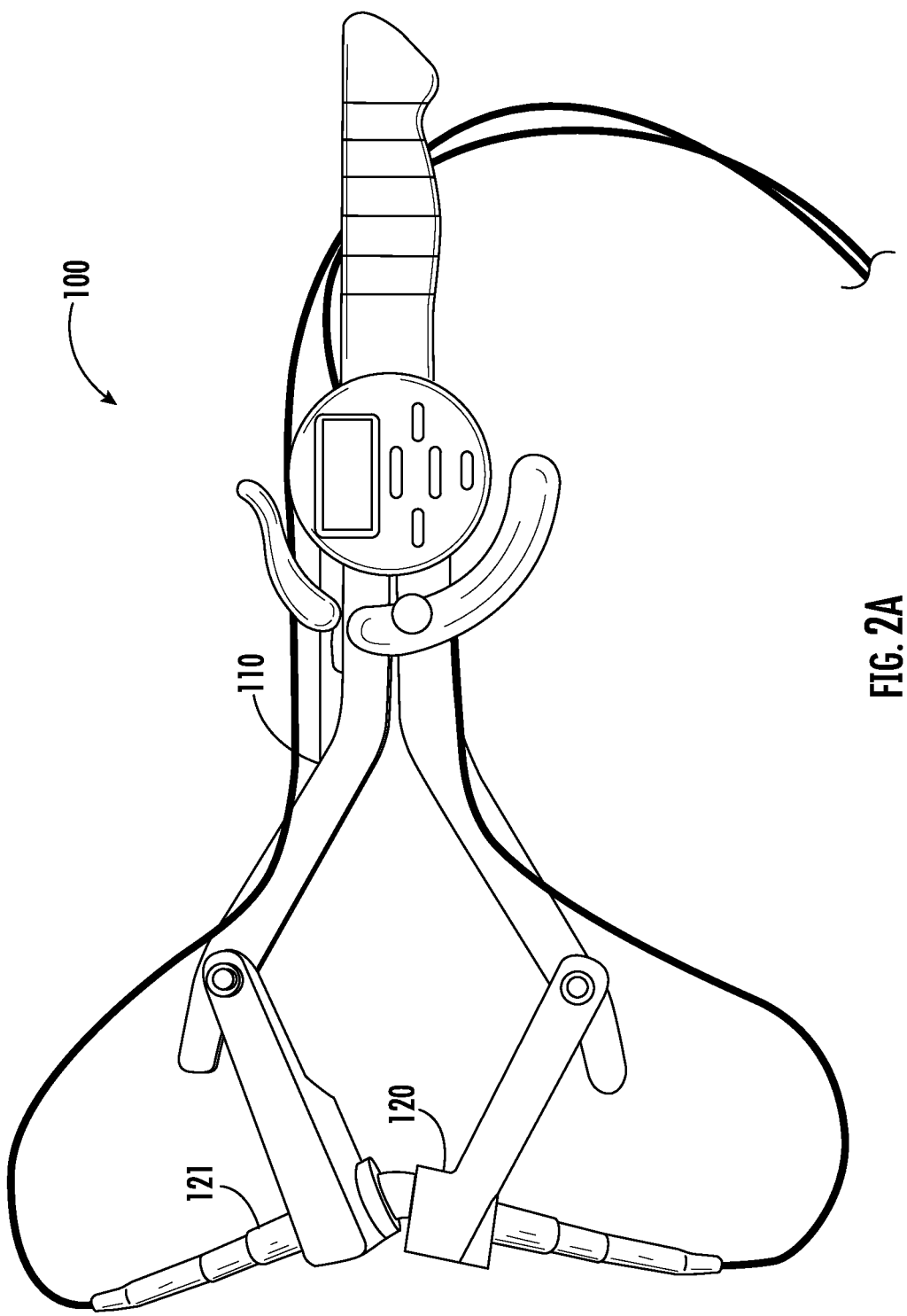
Figure 2B:
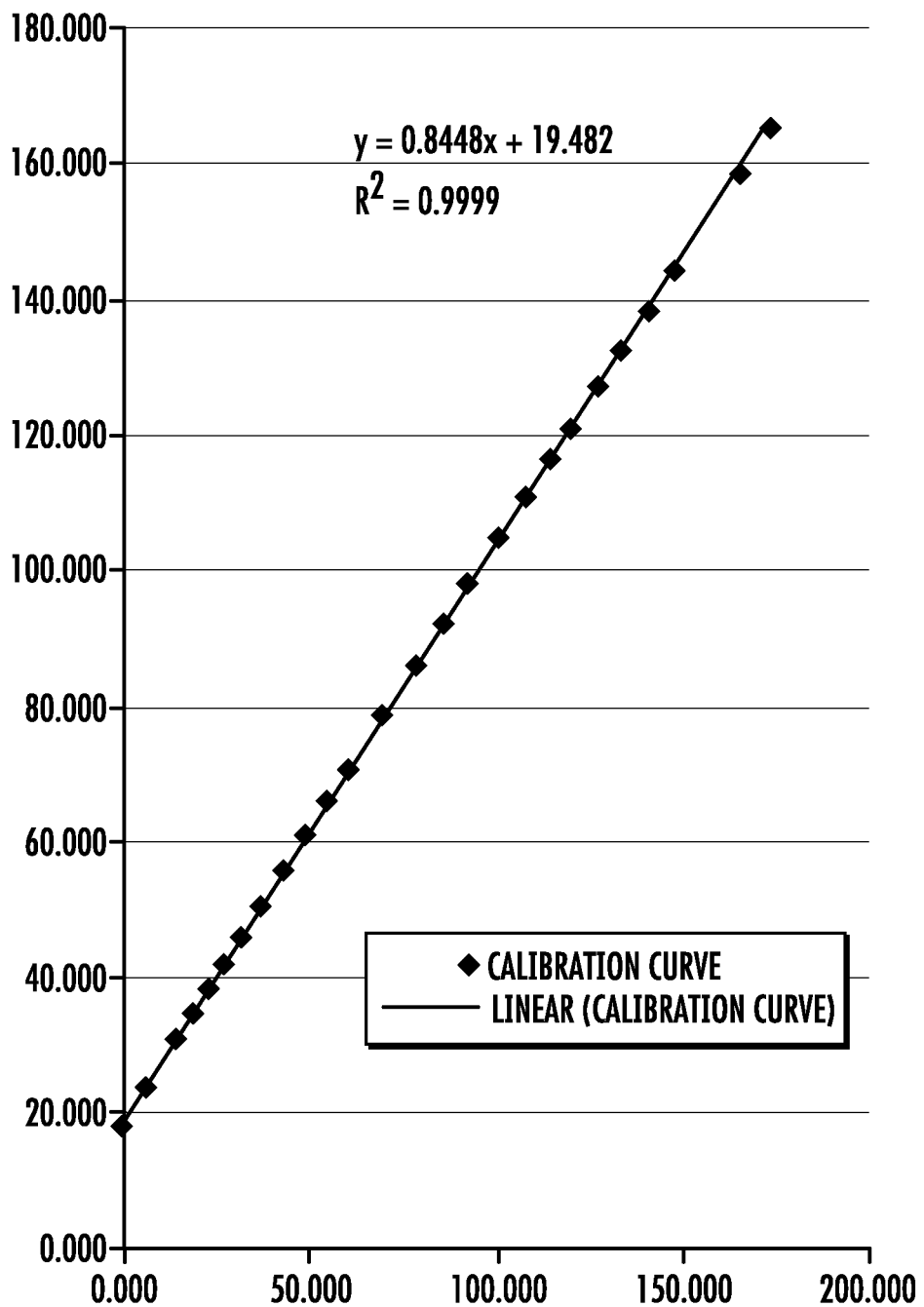
Figure 2C:
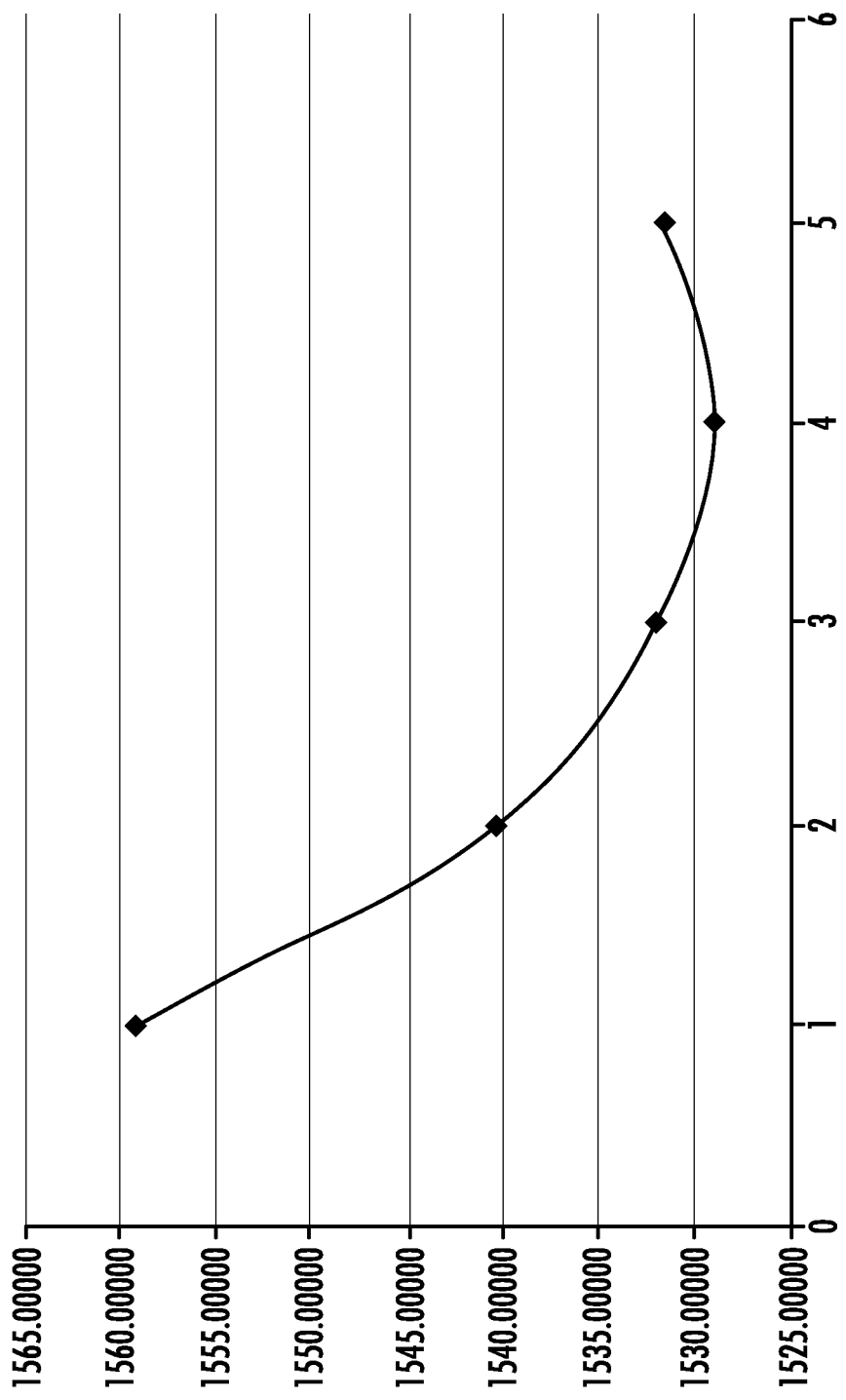

FIG. 2A shows a prototype device according to one embodiment of the present invention. FIG. 2B shows a calibration curve for the device, in which the calculated distance between transducers based on echo times (Y-axis, in mm) is linearly related to the distance between the transducers read out by the caliper (X-axis, in mm) subject to a small (~20 mm) offset due to a space between the transducers when the calipers are fully closed. FIG. 2C shows measured SOS in m/s (Y axis) as measured in a porcine leg model under five conditions characterized by the injection of various quantities of saline. Condition 1: standard (no added saline); Condition 2: 5 mL saline injected; Condition 3:20 mL saline injected; Condition 4: 35 mL saline injected; Condition 5: 50 mL saline injected.

Figure 3:
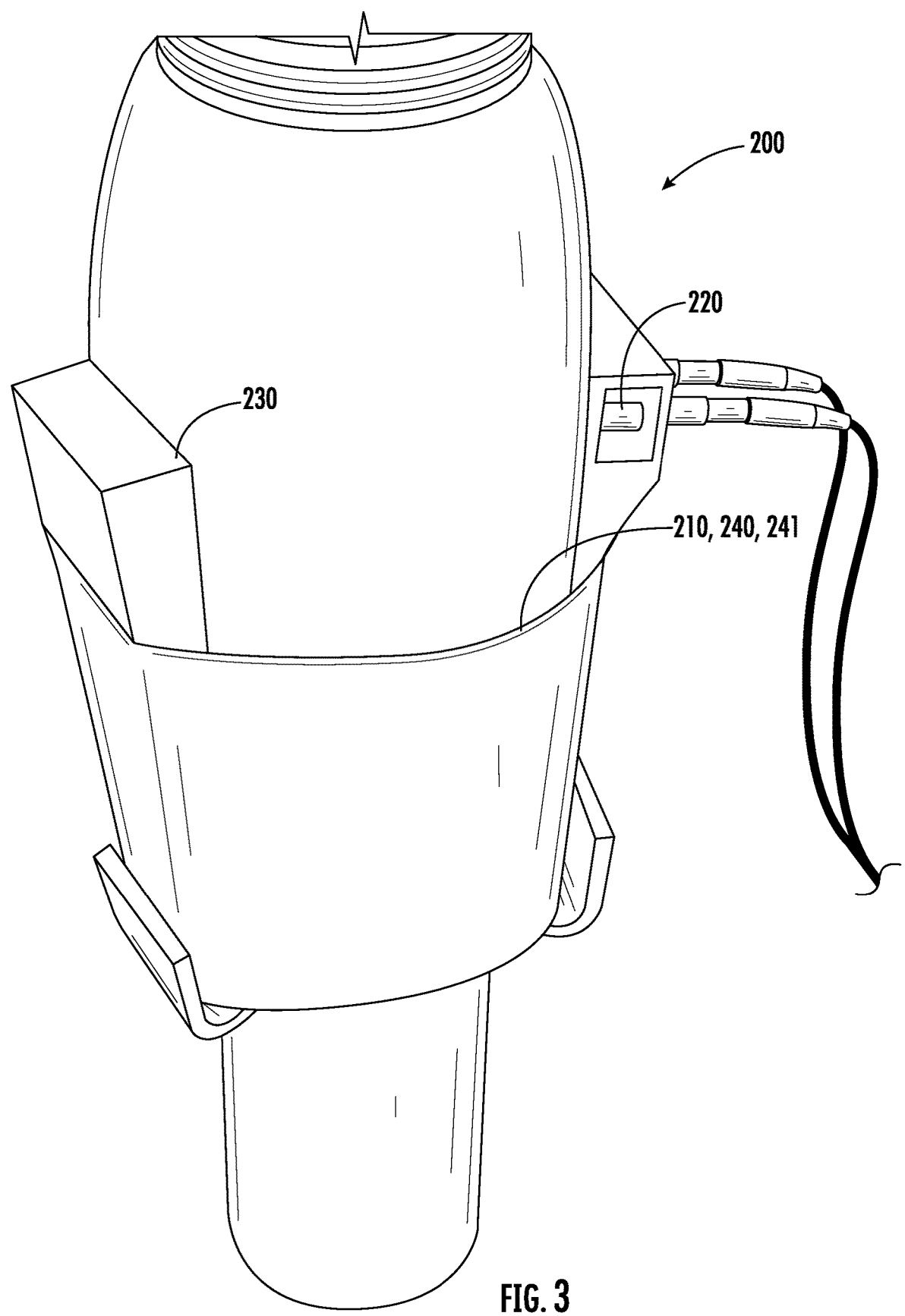

FIG. 3 shows a prototype device according to an embodiment of the present invention.

Figure 4B:
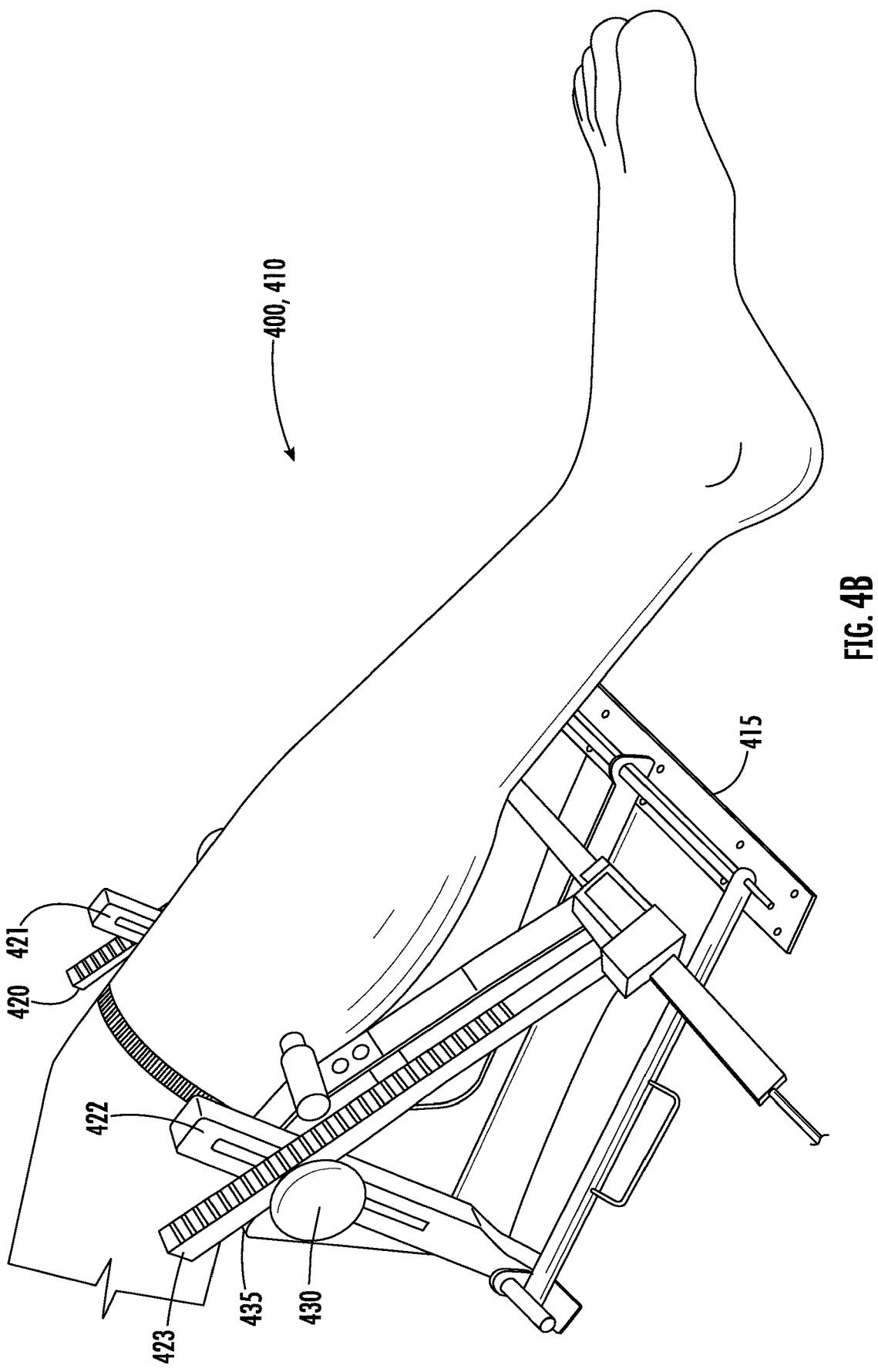

FIGS. 4A and 4B show a prototype device according to an embodiment of the present invention Unless otherwise provided in the following specification, the drawings are not necessarily to scale, with emphasis being placed on illustration of the principles of the invention.

DETAILED DESCRIPTION OF THE PREFERRED EMBODIMENTS

Generally, systems and devices according to the present invention are designed for placement about an extremity, (i.e. an arm or a leg) though in some embodiments the designs and methods disclosed herein can be adapted to measure edemas in the abdominal cavity and the vicinity of the liver, or in the thoracic cavity and the vicinity of the lungs, heart and great vessels by placing elements of the devices disclosed herein about the torso or thorax. For the sake of brevity, the examples presented below focus on devices placed about extremities, but it will be understood by those of skill in the art that the devices, systems and methods of the invention are equally suited to application about the trunk (i.e. the abdomen or thorax) of a patient.

The devices incorporate two or more (and preferably three) ultrasound transducers, and, optionally, at least one pair of skin electrodes for measuring impedance. These elements are held in place and in close apposition with the skin of the extremity by means of a caliper, cuff, or other suitable retention element capable of at least partially enclosing the extremity being measured. The retention element, in addition to securing the transducers and electrodes in close apposition to the skin of the extremity, optionally permits the measurement of a distance between these elements with sufficient precision to calculate ultrasound velocity and/or tissue impedance.

The function of devices and systems according to the present invention is represented schematically in FIG. 1. The method includes 1 transmitting and receiving ultrasound signals through a soft tissue of the body, which may include any non-bony tissue in any portion of the body where a determination of fluid content and/or electrolyte balance is desired. A distance calculation 2 is also performed to establish a distance between the ultrasound source and detector; from these steps 1 and 2 a speed of sound calculation 3 is performed, and the speed of sound value is then used in a fluid content calculation 4. In some cases, an impedance measurement 5 is made through the soft tissue, and the measured impedance is also optionally used to estimate a fluid content 6 of the soft tissue and/or to perform, with the fluid content value established by fluid content calculation 4, an electrolyte balance calculation 7. The results of one or more of the fluid content calculation 4, the fluid content estimate 6, or the electrolyte calculation 7, are included in an output 8 to a health care provider, which concludes the method.

An exemplary device according to the present invention permits, on the one hand, the transmission and receipt of ultrasound signals through the body and measurement of the distance traveled by the ultrasound, thereby permitting the calculation of the speed of sound ("SOS") through the body. The speed of sound, in turn is used to calculate a fluid content of a soft tissue within the body. In addition, the fluid content is calculated based on an impedance measurement. The nature of the fluid content calculation based on an impedance measurement has been shown in the literature to be only valid when the electrolyte status of a patient is normal. Otherwise, the fluid content calculation yields an inaccurate result that includes input from both the true fluid status of the patient and the error associated with the patient's electrolyte imbalance from the normal state. An algorithm for determining electrolyte balance based on ultrasound-measured fluid balance and measured impedance is set out in FIG. 1B. The algorithm begins with an impedance measurement signal 10, which conveys information about the true hydration status 11 of the patient but which also includes a "noise" component 12 due to deviations in electrolyte balance. The electrolyte balance component 12 can be separated from the hydration status component 11 with the benefit of the reference hydration signal 13 established by the ultrasound measurement. That signal 13 is fed into an adjustable filter 14 to generate an electrolyte imbalance signal 15. The electrolyte imbalance signal 15 is fed into an adaptive algorithm along with the a priori hydration signal 13, and the filter 14 is adjusted 17 by the algorithm, thereby refining the electrolyte imbalance signal 15. The electrolyte imbalance signal 15 is then output to a health care provider.

Referring to FIG. 2A, a prototype device 100 includes a caliper 110 and two ultrasound transducers 120, 121, which are positioned to face one another when placed around an extremity. In use, the caliper 110 is opened to permit the insertion of a bodily extremity between the paired ultrasound transducers 120, 121, and then adjusted to place the transducers snugly in contact with the extremity. The angle of the calipers is then noted in order to assess the distance between the transducers 120, 121, both for calibration purposes and subsequent use of the device. An exemplary calibration curve for device 100 is shown in FIG. 2B. In the figure, the Y axis values are those calculated based on SOS and the X axis values being the distance reading from the caliper 110 of the device 100. The units are millimeters on both axes. Because the ultrasound transducers are not perfectly flat, there is an offset of about 20 mm in the calculated distance relative to the distance indicated by the caliper 110.

The speed of sound in pure water at a given temperature and pressure is known and can be used to calibrate the device. Since the speed of sound during calibration is constant, a calibration curve can be generated that records the time of flight for the ultrasonic ping vs the distance between the transducers at various distances and an associated linear model can be fitted. This model fit allows the caliper reading to be transformed to the true distance between the transducers, since the mounting of the transducers may induce small distance offsets to the caliper reading. In addition, a second curve can be generated that compares the caliper reading distance against the distance computed using time of flight of the ultrasonic ping and an a priori known value for the speed of sound.

The calibration was performed with both transducers immersed in DI water and initiating a pulse on one transducer and receiving the acoustic wave on the other at various manually determined distances. The caliper reading, the associated time of flight of the acoustic wave between the transducers and the temperature of the water was recorded.

Once it is calibrated, the device 100 is suitable for use on patients the pulse echo time for signals from each transducer is used to measure SOS through the tissue in the extremity, and thereby provide an estimate of the water content of the extremity. The relationship between SOS and water content as measured using the device 100 in a porcine leg model with known aliquots of fluid injected into the tissue is shown in FIG. 2C.

Separately, and optionally, paired impedance electrodes 130, 131 (not shown) are placed on the body of the patient for the impedance measurement. The electrodes are preferably skin electrodes, given the non-invasive nature of the methods contemplated by the present invention.

Another prototype device according to the present invention is shown in FIG. 3. Device 200 includes a cuff 210 which can be cinched around an extremity and secured, for instance by means of one or more Velcro patches. The cuff 210 may be inflatable to enable and utilize circumferential pressure to align and embed any reflectors or transducers attached to the cuff. The cuff 210 optionally includes markings which can be used to measure a circumference of the extremity onto which device 200 is placed. To the inner surface of the cuff 210, an ultrasound transducer assembly 220 is attached along with an ultrasound reflector assembly 230; at least one of the transducer assembly 220 and the reflector assembly 230 is configured to be moved (for example by sliding, or reversible attachment with Velcro) within the circumference defined by the cuff, so that the transducer assembly 220 and the reflector assembly 230 can be positioned on opposite sides of extremities of different sizes when the device 200 is in use. The device also optionally includes one or more electrodes 240, 241 for impedance measurement, though in some embodiments, one or both of the impedance measurement electrodes 240, 241 are placed on other parts of the body of the patient.

The transducer assembly 220 includes at least two, and preferably three ultrasound transducers. As a general matter, with three transducers, the speed of sound can be calculated without directly measuring the diameter of the extremity, as long as the distance between each transducer is known. Thus, in preferred embodiments, the transducer assembly 220 includes three transducers spaced a fixed distance apart from one another, advantageously eliminating the need to make a mechanical measurement of the distance between transducers. The spacing is preferably sufficiently large to facilitate triangulation of a distance between the each transducer in the transducer assembly 220 and the reflector assembly 230, while at the same time close enough to accommodate the curvature of relatively small-diameter extremities.

In use, the cuff 210 is placed around the extremity of the patient and cinched so that the transducer assembly 220 and the reflector assembly 230 are positioned on opposite sides of the extremity in snug contact with the skin; thereafter, the transducers are energized, echo times are measured and analyzed as shown in FIG. 1 and as discussed above. The preferred embodiment utilizes an inflatable cuff 210 to snugly hold the transducers and reflector against the tissue/skin of the patient, though other embodiments utilize adhesive patches with transducers mounted inside, which may advantageously be left in place for days or weeks without moving. These forms assist in securement, stability, and alignment of the transducers and reflector. If the device 200 includes electrodes 240, 241, these are activated as well, facilitating the determination of electrolyte balance as discussed above.

In some embodiments the speed of sound is measured by means of endogenous bodily sound sources. Some organs such as the heart give off sound (i.e. heart sounds of the valves closing etc.) By placing piezoelectric crystals (and in some cases the same crystals that generate the ultrasonic pulse) against the skin, sounds or vibrations from the body can be passively detected. Because such sounds travel through the body at SOS, it is possible compute the SOS through the tissue if the distance is known precisely. The distance can be measured by the placement of multiple piezo-electric detectors about the body of the patient which are spaced apart at known distances; then a user can triangulate the source of the sound in the same manner as described above and thereby estimate the distances traveled between sound source and detector. For instance, the start time for a time of flight measurement for each detector could be based on an ECG signal or any other suitable starting point.

To improve the reproducibility of ultrasound-based fluid measurements, certain systems and devices according to the present invention include one or more structures to facilitate the consistent placement of one or both of the ultrasound transducer assembly and the reflector assembly, for instance in reference to a fiducial anatomical landmark such as the back of the knee. These systems advantageously limit the variation in tissue composition between measurements, permitting comparison of measurements taken in a single patient over time.

Turning to FIGS. 4A and B, in one example, a system for ultrasound fluid measurement 400 includes a positioning accessory 410 that permits consistent placement of an ultrasound transducer and reflector in reference to the knee. The positioning accessory 410 includes a base 415, to which four crossmembers 420, 421, 422, 423 are coupled, preferably by means of hinges 425, rotating bushings, or another flexible or rotatable connection. On each side of the device, two crossmembers are slidably engaged with one another, preferably by means of a sliding clamp 430 that includes a screw inserted through a slot extending along at least a portion of the length of at least one of the crossmembers. For example, in the positioning accessory 410 pictured in FIGS. 4A and B, each pair of crossmembers 420, 421 and 422, 423, is coupled together by a screw clamp 430 inserted into slots in each crossmember. Alternatively, the screw clamp may be fixedly attached to one of the crossmembers, and may insert through a slot in the corresponding crossmember.

Whichever arrangement is used, each crossmember that has a slot also bears a series of indices, graduations, rules, or other markings extending along a surface of the crossmember for the length of the slot to permit the sliding clamp 430 to be secured at a known position along the length of each slot, and consequently to be secured at a defined height above the base 415.

Each sliding clamp 430 includes a structure for coupling to and/or securing an ultrasound transducer or reflector, or alternatively to an assembly (for example a rigid ring, not shown) that in turn couples to one or more transducers and/or reflectors. For example, in the exemplary system pictured in FIG. 4B, one sliding clamp 430 couples to an ultrasound transducer assembly, which is visible in the photo, and the other sliding clamp 430 couples to a reflector. The positioning accessory 410 also optionally includes a support 435 on which a patient's limb can rest during measurements. The support is, preferably, slidable along a width and/or length of the base 415 and adjustable in height, so it can be quickly adapted for use with patients of different size.

In use, the patient rests a limb (particularly the lower leg) in the positioning accessory 410 and the sliding clamps 430 are adjusted to align them with predetermined markings on the surface of one or more of the crossmembers 420, 421, 422, 423 or, if a patient is using the accessory 410 for the first time, to align the sliding clamps 430 relative to a fiducial anatomical landmark such as the back of the knee. In first-time treatments, once the sliding clamps 430 are secured, their position is recorded by reference to the markings or indices along the length of each slot in the applicable crossmembers 420, 421, 422, 423, to permit rapid configuration of the positioning accessory 410 during future measurements. Once the sliding clamps 430 are positioned, one or more transducers and reflectors are placed in contact with the limb of the patient, and the measurement is made.

Figure 1A:
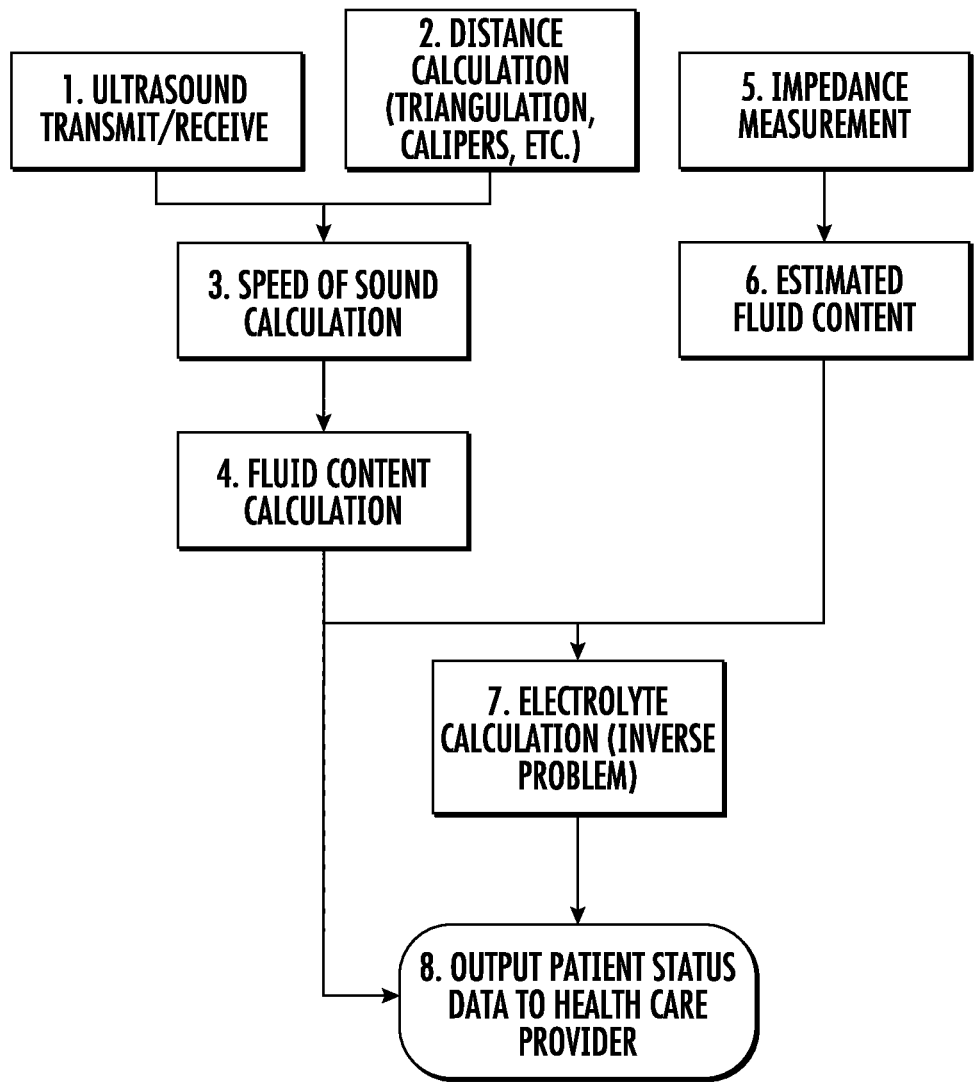
FIG. 1A is a schematic depiction of a method of assessing the fluid volume and electrolyte balance of a patient according to the present invention.
Figure 1B:
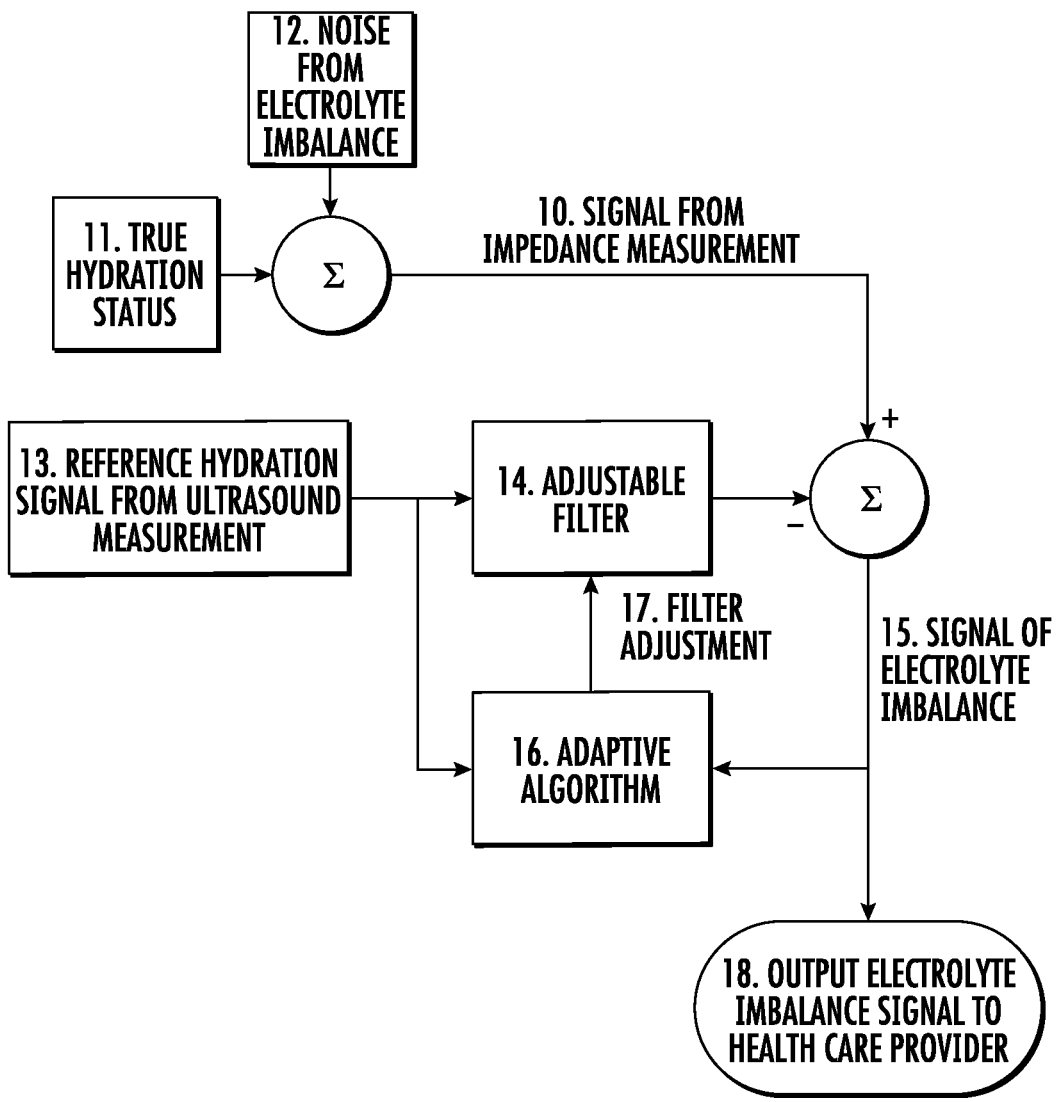
FIG. 1B is a schematic depiction of a sub-method of assessing electrolyte balance using fluid balance data and measured impedance.

It should also be appreciated that, while the prototype devices shown in the figures utilize wired connections to relay data from ultrasound transducers to the processor, any suitable connection, wired or wireless, may be used to transmit signals between ultrasound transducers, processors configured to perform the fluid and electrolyte balance heuristics described in FIGS. 1A and B, and display or output devices such as monitors, etc. Where wireless connections are used, any suitable protocol, such as Bluetooth, WiFi, etc. can be used, and data may be transmitted over local or wide area networks, or over the internet, for instance to a cloud based patient data management platform such as Latitude™ (Boston Scientific Corporation, Marlbourgh, Mass.).

The phrase "and/or," as used herein should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

The term "consists essentially of means excluding other materials that contribute to function, unless otherwise defined herein. Nonetheless, such other materials may be present, collectively or individually, in trace amounts.

As used in this specification, the term "substantially" or "approximately" means plus or minus 10% (e.g., by weight or by volume), and in some embodiments, plus or minus 5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

Certain embodiments of the present invention have described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

What is claimed is:

1. A system comprising:
a transducer assembly including three ultrasound transducers spaced a fixed distance apart from one another and configured to produce a plurality of echoes;
a retention element housing the transducer assembly and configured to surround at least a portion of a circumference of a soft tissue of a patient;
an ultrasound reflector, coupled to the retention element and configured for placement proximate the soft tissue of the patient, the ultrasound reflector positioned opposite the transducer assembly and configured to reflect the plurality of echoes; and
a processor configured to calculate a diameter of the soft tissue of the patient by triangulating distances between the ultrasound reflector and each of the three ultrasound transducers based on a plurality of echo times measured by the three ultrasound transducers.

2. The system of claim 1, wherein the retention element is a cuff sized to be placed about the circumference of the soft tissue of the patient.

3. The system of claim 1, wherein the retention element is selected from the group consisting of one or more adhesive patches and a caliper.

4. The system of claim 1, wherein:
(a) the retention element is or connects to a positioning accessory comprising: a base, a plurality of crossmembers, each rotatably or flexibly coupled to opposite ends of the base, and a moveable clamp for coupling at least two of the plurality of crossmembers to one another; and
(b) at least one of the crossmembers includes a slot through which the moveable clamp is insertable and a plurality of markings along a length of the slot.

5. The system of claim 1, further comprising a plurality of impedance measurement electrodes.

6. The system of claim 5, wherein the retention element is connected to the plurality of impedance measurement electrodes.

7. The system of claim 1, wherein the ultrasound reflector is slidably disposed along an interior of the retention element.

8. A method of assessing a patient, the method comprising:
calibrating an ultrasound system comprising a device comprising a transducer assembly including three ultrasound transducers, and an ultrasound reflector opposite the transducer assembly to determine relative distances between each of the three ultrasound transducers of the transducer assembly and the ultrasound reflector;
measuring, using ultrasound, a speed of sound through a soft tissue of the patient; and
calculating, based on the speed of sound, a fluid content of the tissue;
wherein calibrating includes:
placing the device comprising the transducer assembly about at least a portion of a circumference of the soft tissue of the patient, the ultrasound transducers being separated from one another by a fixed distance;
positioning the ultrasound reflector opposite the three ultrasound transducers of the transducer assembly;
energizing the three ultrasound transducers to produce a plurality of ultrasound echoes and measure a plurality of ultrasound echo times;
calculating, based on the ultrasound echo times and the at least one fixed distance, distances between each of the three ultrasound transducers and the ultrasound reflector, by triangulating the plurality of ultrasound echoes; and
determining a diameter of the soft tissue in response to the distances between each of the three ultrasound transducers and the ultrasound reflector.

9. The method of claim 8, wherein the device is a cuff.

10. The method of claim 8, wherein the device includes an adhesive pad.

11. The method of claim 8, wherein the ultrasound reflector is moveable within the device relative to the ultrasound transducers.

12. The method of claim 11, further comprising placing the reflector opposite the three ultrasound transducers about the soft tissue.

13. A method of assessing a patient, the method comprising:
calibrating an ultrasound system comprising a device comprising a transducer assembly including three ultrasound transducers and an ultrasound reflector opposite the transducer assembly to determine relative distances between each of the three ultrasound transducers of the transducer assembly and the ultrasound reflector;
energizing the three ultrasound transducers to produce a plurality of ultrasound echoes and measure a plurality of ultrasound echo times;
calculating, based on the ultrasound echo times, distances between each of the three ultrasound transducers and the ultrasound reflector by triangulating the plurality of ultrasound echo times;
determining a diameter of a soft tissue in response to the distances between each of the three ultrasound transducers and the ultrasound reflector;
measuring a speed of sound through the soft tissue via a processor;
estimating a fluid content of the soft tissue based on the speed of sound through the soft tissue via the processor;
measuring a tissue impedance; and
based on the estimated fluid content, the diameter, and the measured tissue impedance, estimating an electrolyte content of the soft tissue via the processor;
wherein measuring a speed of sound through the tissue includes detecting a sound generated by the body of the patient using a plurality of piezoelectric detectors on a surface of the body on the patient, each of the plurality of piezoelectric detectors being separated from one another by a fixed distance.

14. The method of claim 13, further comprising detecting an event within the body of the patient which generates the sound.

15. The method of claim 14, wherein the event is inside of the heart of the patient.

16. The method according to claim 13, wherein estimating an electrolyte content of the tissue includes the application of an adaptive algorithm.

\* \* \* \* \*